(12) United States Patent
Stokes et al.

(10) Patent No.: US 10,583,441 B2
(45) Date of Patent: Mar. 10, 2020

(54) SELF-SEALING PIPETTE SEPTUM

(71) Applicant: Nabsys 2.0 LLC, Providence, RI (US)

(72) Inventors: Jeffrey H. Stokes, Harvard, MA (US); Ryan C. Almeida, Saunderstown, RI (US)

(73) Assignee: NABSYS 2.0 LLC, Providence, RI (US)

( * ) Notice: Subject to any disclaimer, the term of this patent is extended or adjusted under 35 U.S.C. 154(b) by 0 days.

(21) Appl. No.: 14/852,086

(22) Filed: Sep. 11, 2015

(65) Prior Publication Data

US 2016/0074866 A1 Mar. 17, 2016

Related U.S. Application Data

(60) Provisional application No. 62/049,165, filed on Sep. 11, 2014.

(51) Int. Cl.
*B01L 3/00* (2006.01)
*A61J 1/14* (2006.01)
(Continued)

(52) U.S. Cl.
CPC ............ *B01L 3/565* (2013.01); *A61J 1/1406* (2013.01); *A61M 39/045* (2013.01);
(Continued)

(58) Field of Classification Search
CPC .. A61M 2039/0093; A61M 2039/0072; A61M 2039/0081; A61M 2039/009; A61M 39/045; A61J 1/1406
See application file for complete search history.

(56) References Cited

U.S. PATENT DOCUMENTS 5,989,224 A * 11/1999 Exline ................ A61B 17/3462
604/167.02
6,497,138 B1 * 12/2002 Abdel-Rahman .... G01N 30/466
73/23.26
(Continued)

FOREIGN PATENT DOCUMENTS

WO    WO-02066595 A1    8/2002

OTHER PUBLICATIONS

International Search Report and Written Opinion for International Patent Application No. PCT/US2015/049762 dated Feb. 8, 2016 (19 Pages).
(Continued)

*Primary Examiner* — Justin N Olamit
(74) *Attorney, Agent, or Firm* — Goodwin Procter LLP

(57) ABSTRACT

A liquid injection port including a liquid input block defining a liquid input conduit; a compression block adapted to mate with the liquid input block; and a septum including a deformable material mounted in a septum retainer, the septum defining a central perforation, and forming a seal between the liquid input block and the compression block. The septum defines a conical deformation toward the liquid input conduit. A method for delivering fluid from a pipette tip includes a) introducing the fluid into the pipette tip; b) inserting the pipette tip into a pipette conduit defined by a compression block; c) inserting the pipette tip through a septum mounted in the compression block; and d) releasing the fluid in the pipette tip into a liquid input conduit defined in a liquid input block, the septum defining a conical deformation toward the liquid input conduit while maintaining a seal.

17 Claims, 8 Drawing Sheets

(51) Int. Cl.
    *A61M 39/04*     (2006.01)
    *G01N 1/28*     (2006.01)
    *A61M 39/00*     (2006.01)

(52) U.S. Cl.
    CPC ........... B01L 3/50825 (2013.01); B01L 3/561 (2013.01); G01N 1/28 (2013.01); *A61M 2039/0063* (2013.01); *A61M 2039/0072* (2013.01); *A61M 2039/0081* (2013.01); *B01L 2200/0689* (2013.01); *B01L 2300/044* (2013.01); *B01L 2300/123* (2013.01)

(56) References Cited

U.S. PATENT DOCUMENTS

| | | | |
|---|---|---|---|
| 7,257,987 B2 * | 8/2007 | O'Brien | G01N 1/2202 73/23.22 |
| 8,377,039 B2 * | 2/2013 | Utterberg | A61M 39/02 604/533 |
| 8,805,478 B2 * | 8/2014 | Powers | A61M 39/0208 600/427 |
| 8,858,233 B2 * | 10/2014 | Speiser | G09B 23/285 434/219 |
| 2002/0131902 A1 | 9/2002 | Levy | |
| 2003/0208165 A1 | 11/2003 | Christensen et al. | |
| 2009/0216216 A1 * | 8/2009 | Powers | A61M 39/0208 604/506 |
| 2013/0085473 A1 | 4/2013 | Weilbacher et al. | |
| 2014/0224356 A1 * | 8/2014 | Hatton | B65D 47/2031 137/522 |

OTHER PUBLICATIONS

International Preliminary Report and Written Opinion dated Mar. 23, 2017, PCT/US2015/049765, 13 pages.

* cited by examiner

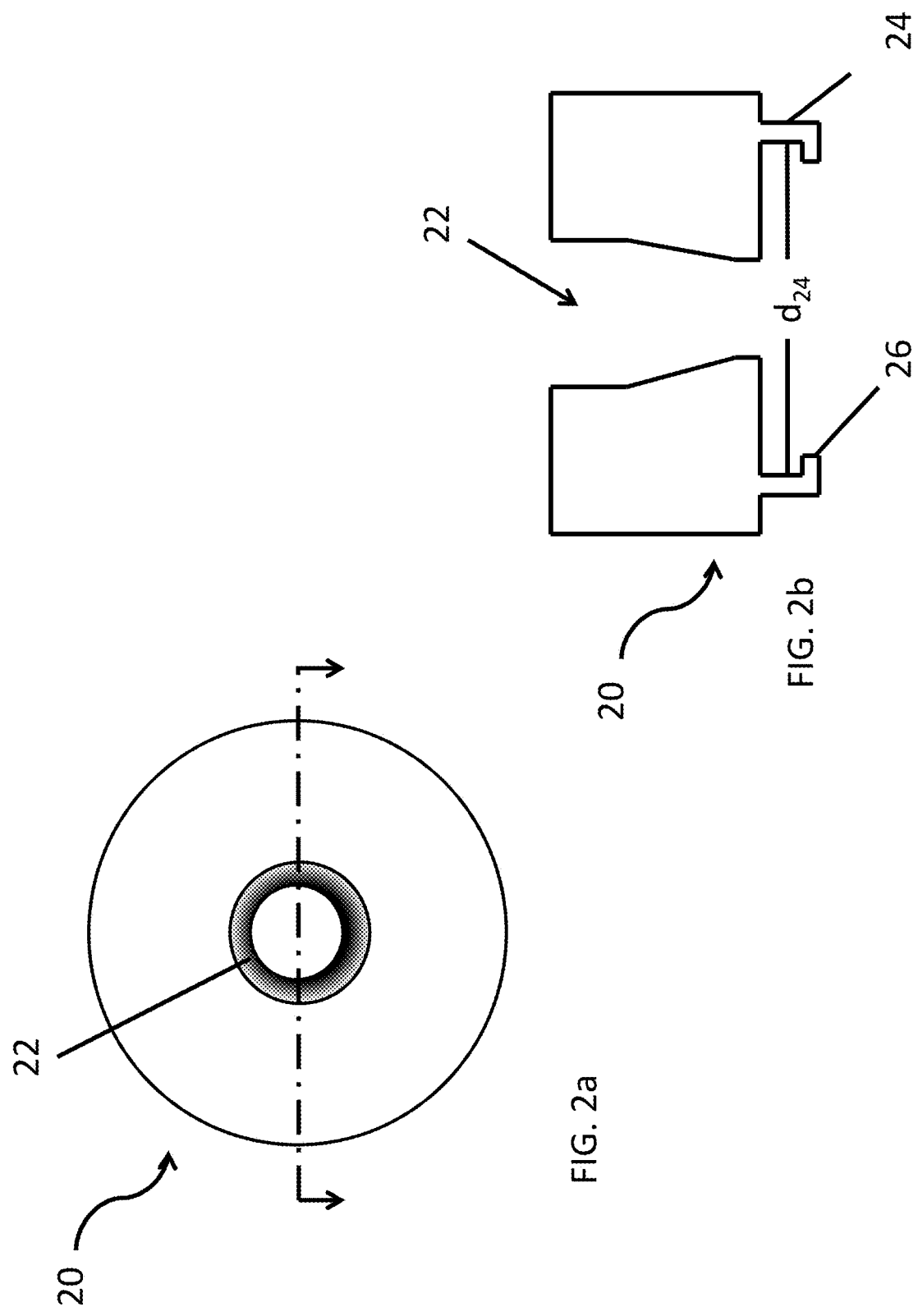

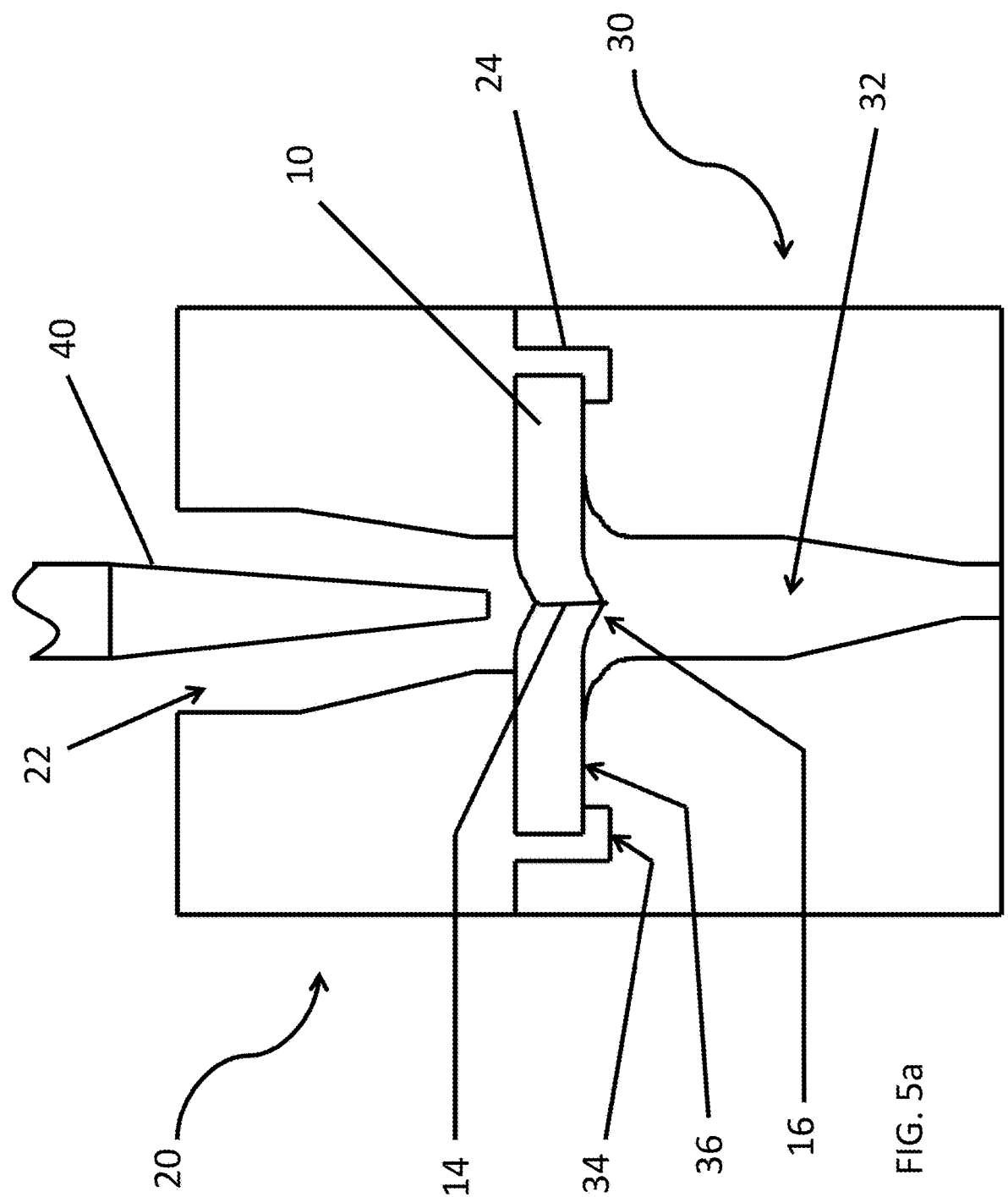

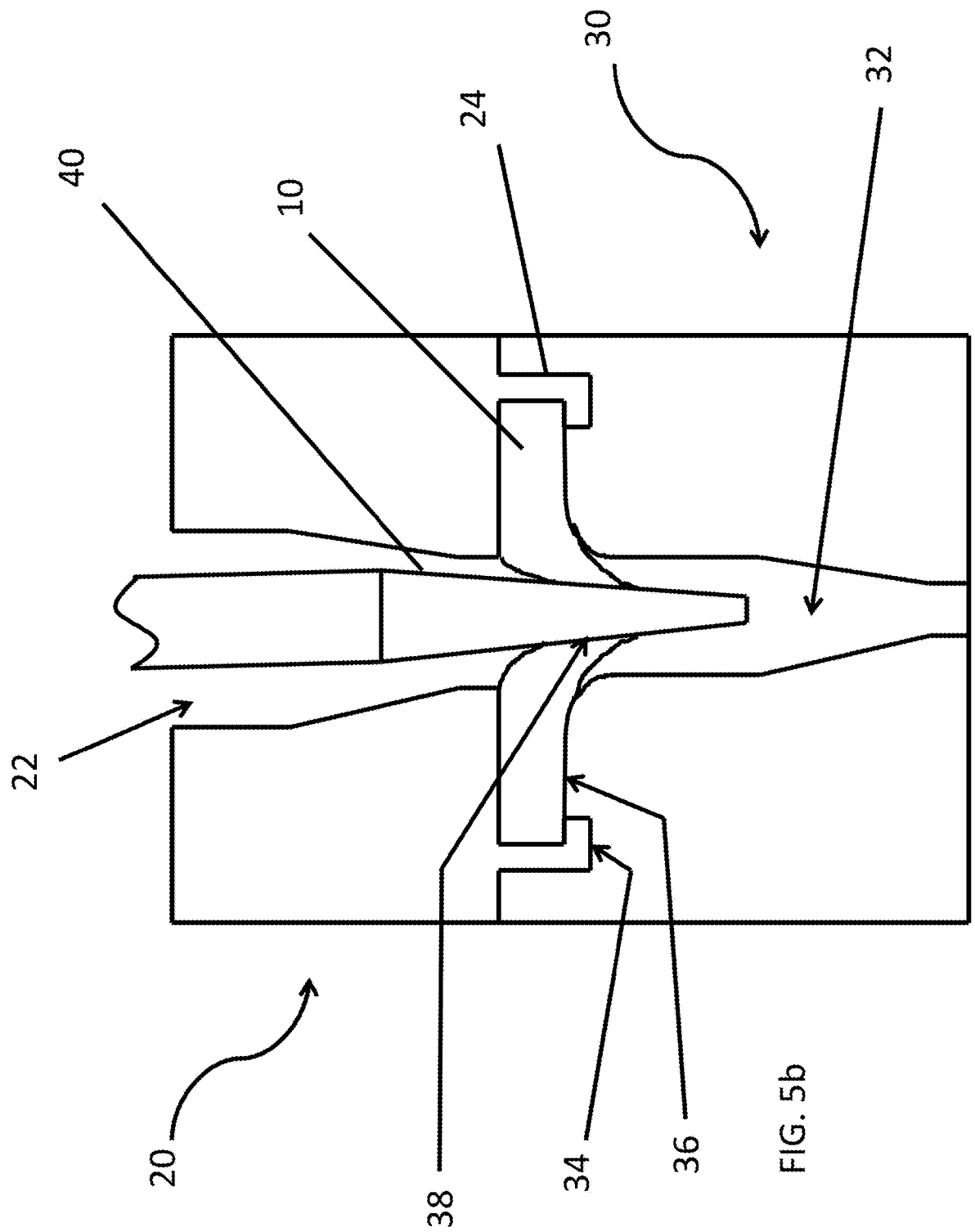

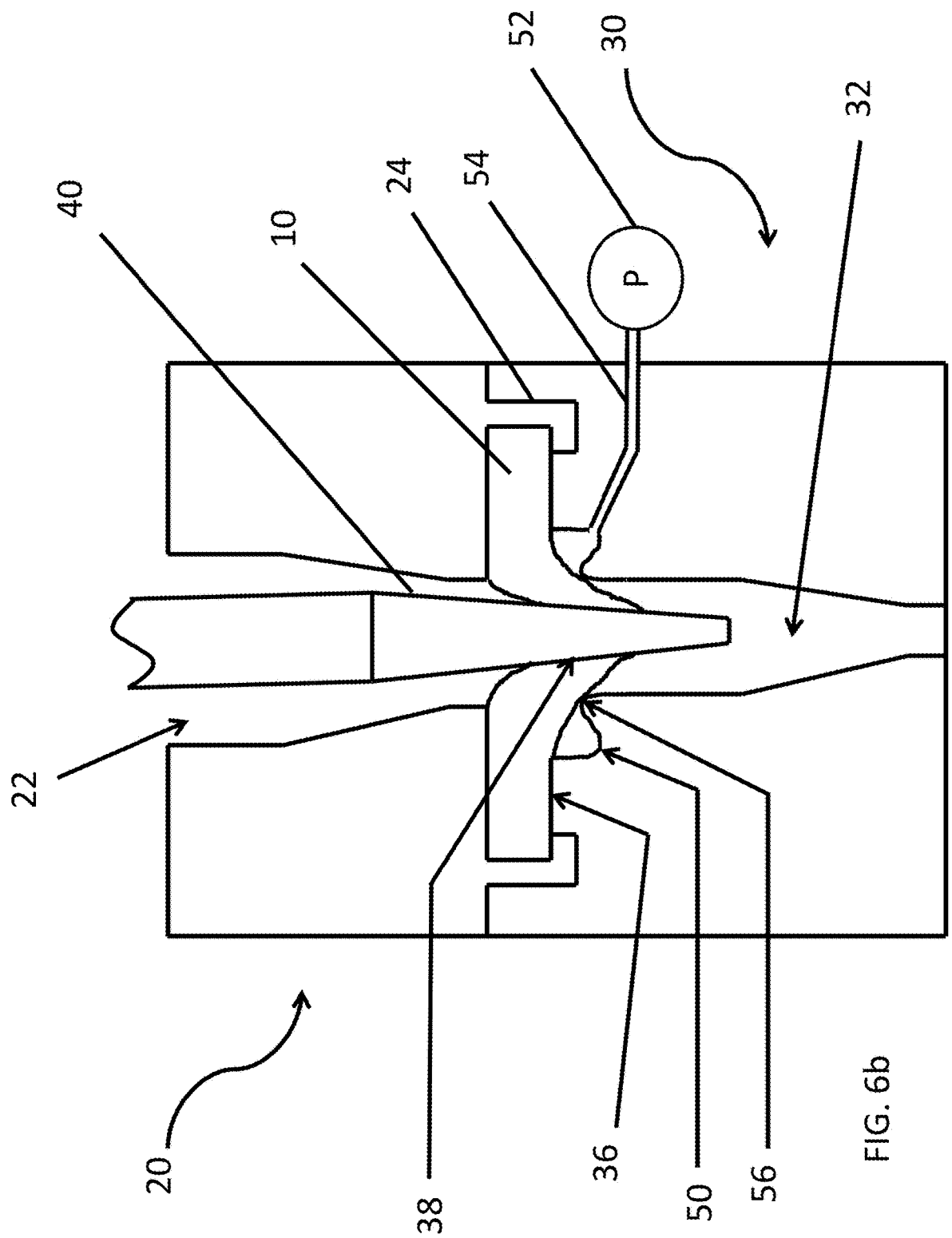

SELF-SEALING PIPETTE SEPTUM

RELATED APPLICATION

This application claims the benefit of priority to U.S. Provisional Application Ser. No. 62/049,165 filed Sep. 11, 2014, which is incorporated herein by reference in its entirety.

BACKGROUND

Many biological assays are carried out with liquids being introduced or retrieved by hand pipetting or by using liquid handling robots that inject liquids into or retrieve liquids from numerous assay devices. While self-sealing septa designs for use in these systems exist, many of them suffer from being overly complicated or less than fully effective at making and maintaining a seal over numerous uses. Thus, a need exists for a simple self-sealing design that offers a reliable, long-term, multi-use seal.

SUMMARY

Embodiments of the invention relate to a septum for use in liquid processing devices in which liquid is introduced via, e.g., a pipette. Self-sealing septa are used in liquid handling systems to form a seal, isolating the interior of the apparatus from the outside environment. The seal may be maintained when a dispensing device, such as a pipette, is used to introduce liquid across the septum, and is further maintained once the dispensing device is withdrawn.

In an aspect, embodiments of the invention include a liquid injection port for a liquid processing device, the liquid injection port including a liquid input block defining a liquid input conduit. A compression block is adapted to mate with a top surface of the liquid input block, the compression block defining i) a pipette conduit therethrough aligned with the liquid input conduit; and ii) a septum retainer having an internal diameter. A septum is mounted in the septum retainer, the septum including a deformable material and including a central perforation therethrough to allow a fluid to be introduced across the perforation. The septum forms a seal between the liquid input block and the compression block. When mounted in the septum retainer, the septum defines, at the central perforation, a conical deformation toward the liquid input conduit while maintaining a seal between the liquid input conduit and the pipette conduit.

In certain embodiments, e.g., prior to disposing the septum in the liquid injection port, the septum may have a diameter larger than the internal diameter of the septum retainer, and the central perforation may be defined without removal of the deformable material from the septum retainer. The deformability of the septum and the definition of the central perforation without removal of material may enable a pipette tip to pass through the septum to allow introduction of a liquid into the liquid input conduit while maintaining a seal between the pipette tip and sidewalls of the central perforation.

The deformable material may include an elastomeric material, such as silicone.

A pressurized fluid source may be in fluidic communication with a backside of the septum. The pressurized fluid source may be adapted to deliver up to 100 psi of a pressurized fluid to the backside of the septum. The pressurized fluid source may be adapted to deliver a pressurized fluid such as compressed air, helium, nitrogen, argon, and/or water to the backside of the septum.

In another aspect, embodiments of the invention may include a method for delivering a fluid from a pipette tip, the method including introducing the fluid into the pipette tip. The pipette tip is inserted into a pipette conduit defined by a compression block, and is inserted through a central perforation defined by a septum mounted in a bottom portion of the compression block. The fluid is released in the pipette tip into a liquid input conduit defined in a liquid input block, the liquid input conduit being aligned with the pipette conduit. The septum defines, at the central perforation, a conical deformation toward the liquid input conduit while maintaining a seal between the liquid input conduit and the pipette conduit.

In certain embodiments, the pipette tip forms a seal with the perforation when inserted through the perforation. The pipette tip may be withdrawn from the perforation, with the perforation healing after the pipette tip is withdrawn.

The pipette tip may be withdrawn from the perforation after releasing the fluid, and the introduction, insertion, and release steps repeated. Repeating these steps may include using a second pipette tip. A pressurized fluid, such as compressed air, helium, nitrogen, argon, and/or water, may be delivered to a backside of the septum to facilitate movement of the fluid into the liquid input conduit.

BRIEF DESCRIPTION OF THE DRAWINGS

FIG. 2a is a schematic top view depiction of a compression block in accordance with an embodiment of the present invention.

FIG. 2b is a schematic cut-away side view depiction of one embodiment of a compression block of the present invention.

FIG. 3a is a schematic top view depiction of one embodiment of a liquid input block of the present invention.

FIG. 3b is a schematic cut-away side view of the liquid input block depicted in FIG. 3a.

FIG. 5a is a schematic depiction of one embodiment of a liquid injection port having a compression block mounted septum sealingly engaged with a liquid inlet block, in accordance with an embodiment of the invention.

FIG. 5b is a schematic depiction of the liquid injection port of FIG. 5a having a pipette engaging the septum.

FIG. 6b is a schematic depiction of the liquid injection port of FIG. 6a having a pipette engaging the septum.

DETAILED DESCRIPTION

Some embodiments of the present invention relate to an injection port for a liquid processing device having a self-sealing septum. The injection port is particularly well adapted for use with liquid handling robots, although the invention is not intended to be limited to robotic applications. More specifically, some embodiments of the present invention relate to a septum that maintains an environmental seal through a liquid injection port prior to, during, and after injection of liquid therethrough.

Figure 1:
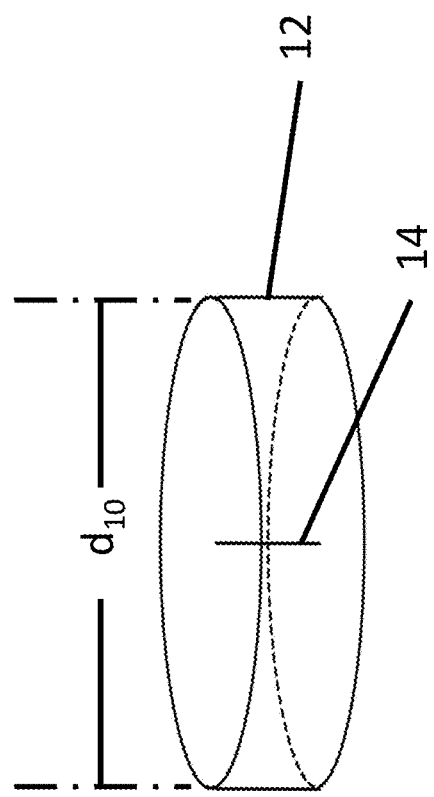
FIG. 1 is a schematic depiction of one embodiment of a septum of the present invention.

FIG. 1 is a schematic depiction of a septum 10 that may be used with embodiments of the present invention. The septum may be a disk, e.g., a circular disk 12 formed of a resilient deformable material, e.g., an elastomeric material such as a silicone elastomer, e.g., a high-purity silicone rubber sheet, 55A Durometer, platinum cured, FDA-compliant and meeting USP Class VI, available from McMaster Carr.

Silicone sheet material has several qualities that make it especially suitable for forming the septum, including its chemical compatibility with various corrosive buffers and its non-toxicity. Also, it is easily stretched. Thus, a perforation 14 located at the septum's center may have smaller dimensions than that of a liquid dispensing device, such as a pipette tip, that is to be inserted through the perforation. In use, the perforation may stretch to the needed diameter without tearing, and then fully recover. Further, the stretchiness of the material allows the septum to stretch while the tip is sliding across the surface to find the opening. Moreover, a material having a slippery surface, i.e., having a low coefficient of friction is preferred as it allows, e.g., a pipette tip to easily enter and exit the septum, reducing wear. The slippery surface of a material such as silicone promotes a good life over hundreds or thousands of piercings by a pipette tip. Even after the silicone starts to wear, it typically remains soft enough to continue to seal. The slippery surface also facilitates the sliding of an end of a pipette tip across the surface of the silicone to find and enter a conical depression 16 (see FIG. 5a) defined by the septum. A less slippery material may grab the end of the pipette tip, not allowing it to find the opening, thereby possibly crushing the tip or else the tip may pierce the septum with the tip. The softness of the material allows a superior seal around the outer diameter of the tip and allows resealing or healing.

While it may have any of a wide range of dimensions, in one embodiment, the septum 10 has a diameter $d_{10}$ of between, 6.5 and 9.5 mm, preferably e.g., 7.9 and 8.1 mm and a thickness of between about 0.5 and 2 mm, preferably between about 1.0 and 1.5 mm. The septum includes a perforation 14 located at its center and extending entirely therethough. Preferably the perforation 14 is defined by deforming the septum, e.g., by cutting a clean slit, i.e., perforation, through the center of the septum with a sharp flat blade having a width of, e.g., between 0.75 and 0.80 mm. The perforation may also be formed by a needle or other small-diameter, sharp object. The perforation may be cut before or after assembly, but may be more reproducibly formed if cut prior to assembly, and not by removing any material from the septum disk. The perforation preferably seals closed when the instrument forming the perforation is removed, i.e., the septum heals itself. Because the perforation length is relatively short, the misalignment of the two halves of the perforation may be minimized, thereby promoting a good seal. The perforation can typically withstand many hundreds of PSI pressure because the perforation's exposed surface area is relatively small, the softness of the material provides a good seal, and the radial compression imparted by the septum retainer keeps the perforation closed. It also is somewhat accommodating of debris from wear and external sources: because it is relatively soft, debris up to a certain size may be embedded into the surface and still allow a seal.

FIGS. 2a and 2b are top and side views, respectively, of a compression block 20. The compression block is preferably formed of any rigid material mechanically capable of supporting radial compression of the septum and withstanding pressurization. A suitable material may be a polymer that is chemically compatible, i.e., does not react, with a sample to be tested, such as polycarbonate ("PC"), polyethylene ("PE"), acrylic, tetrafluoroethylene ("TFE"), polyether ether ketone ("PEEK"), polyphenylene sulfide ("PPS"), etc. The component may be machined, molded, or made by 3D printing, e.g., by a stereo lithography apparatus ("SLA") with a polycarbonate-like UV curable resin material from the SLA supplier. In addition to polymers, other materials may be used, such as metals like stainless steel, aluminum, titanium, etc.

Referring to FIG. 2a, the compression block defines a cylindrical pipette conduit 22 extending therethrough. The pipette conduit 22 preferably has a diameter designed to accommodate any of a wide range of dispensing devices, e.g., pipettes currently employed by fluid handling robots, as well as pipettes used with hand pipetting operations as well. It is preferred, although not required, that the pipette conduit taper to a smaller diameter as it passes through the compression block. Pipette tips typically taper, so a diameter of the pipette tip typically varies along its length, e.g., ranging from 1 mm to 7 mm. A diameter $d_{22}$ of the pipette conduit may have a matching taper. If the pipette conduit is cylindrical, it needs only to be larger than the pipette tip's diameter at the penetration depth to allow penetration desired and to prevent the pipette tip from jamming in the pipette conduit, e.g., pipette conduit diameter $d_{22}$ may be selected from a range of, e.g., 2 mm to 8 mm. Very little leeway between a pipette tip and a sidewall of the pipette conduit is preferable, but not a requirement. For a robotic application, if the robot is properly taught and precise, the pipette tip does not need to be guided by a sidewall of the pipette conduit. However, because pipette tips are typically molded, there may be variations between tips. Thus, even the best taught and precise robot may benefit from guidance. The more guidance is provided for the pipette tip, the longer the life of the septum because the tip then hits the perforation with little contact to the remainder of the septum. The smaller the diameter $d_{22}$, the less out of alignment the tip can be. The pipette conduit sidewall provides coarse guidance, and the conical feature defined by the septum provides fine guidance.

Referring to FIG. 2b, the compression block may also include a septum retainer 24 extending from a bottom portion of the compression block. The septum retainer includes a wall surrounding the pipette conduit and defining a retention lip 26. For use with a circular septum, the wall preferably defines an annular structure. The septum retainer has an internal diameter $d_{24}$ that is preferably smaller than the diameter $d_{10}$ of the septum 10 depicted in FIG. 1. In one embodiment, the septum has a diameter $d_{10}$ of 8 mm and the septum retainer internal diameter $d_{24}$ is 7.5 mm. In a preferred embodiment, the diameter $d_{24}$ of the septum retainer is between about 7.4 and 7.6 mm. The distance between the retention lip 26 and the bottom of the compression block is preferably on the same order as a thickness of the septum 10, described previously.

Figures 3A, 3B:
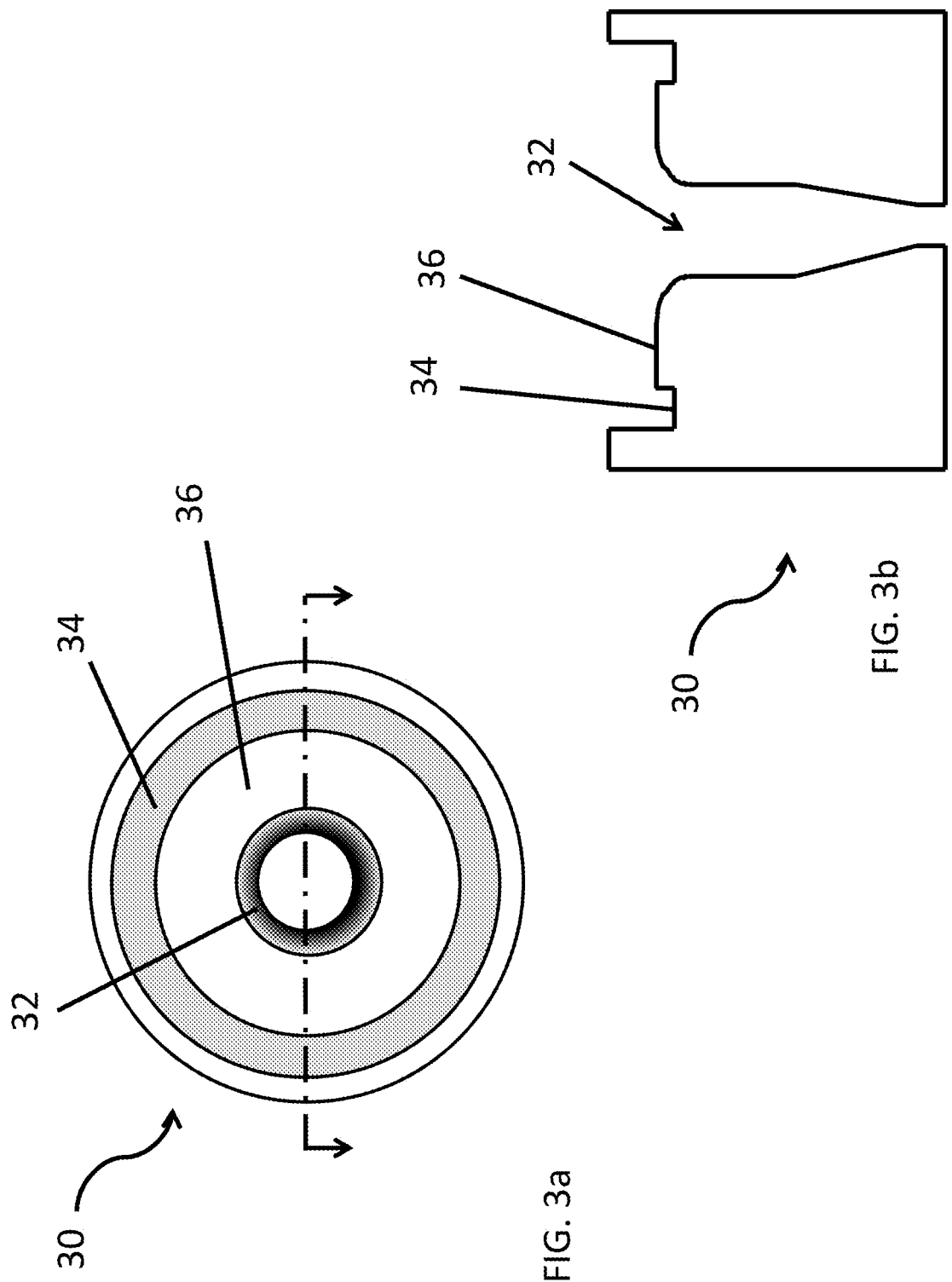

FIGS. 3a and 3b are top and side views, respectively, of a liquid input block 30. The liquid input block is preferably formed of a rigid material, such as any of the polymers and metals discussed above with respect to the compression block. The liquid input block defines a liquid input conduit 32, a septum retainer seat 34 and a sealing surface 36. Both the retainer seat 34 and the sealing surface 36 concentrically surround the liquid input conduit. The retainer seat 34 preferably has a diameter and width suitable for accommodating the retention lip 26 of the compression block 20. As may be seen in FIG. 3b, the septum retainer seat 34 is recessed below the sealing surface 36.

Figure 4:
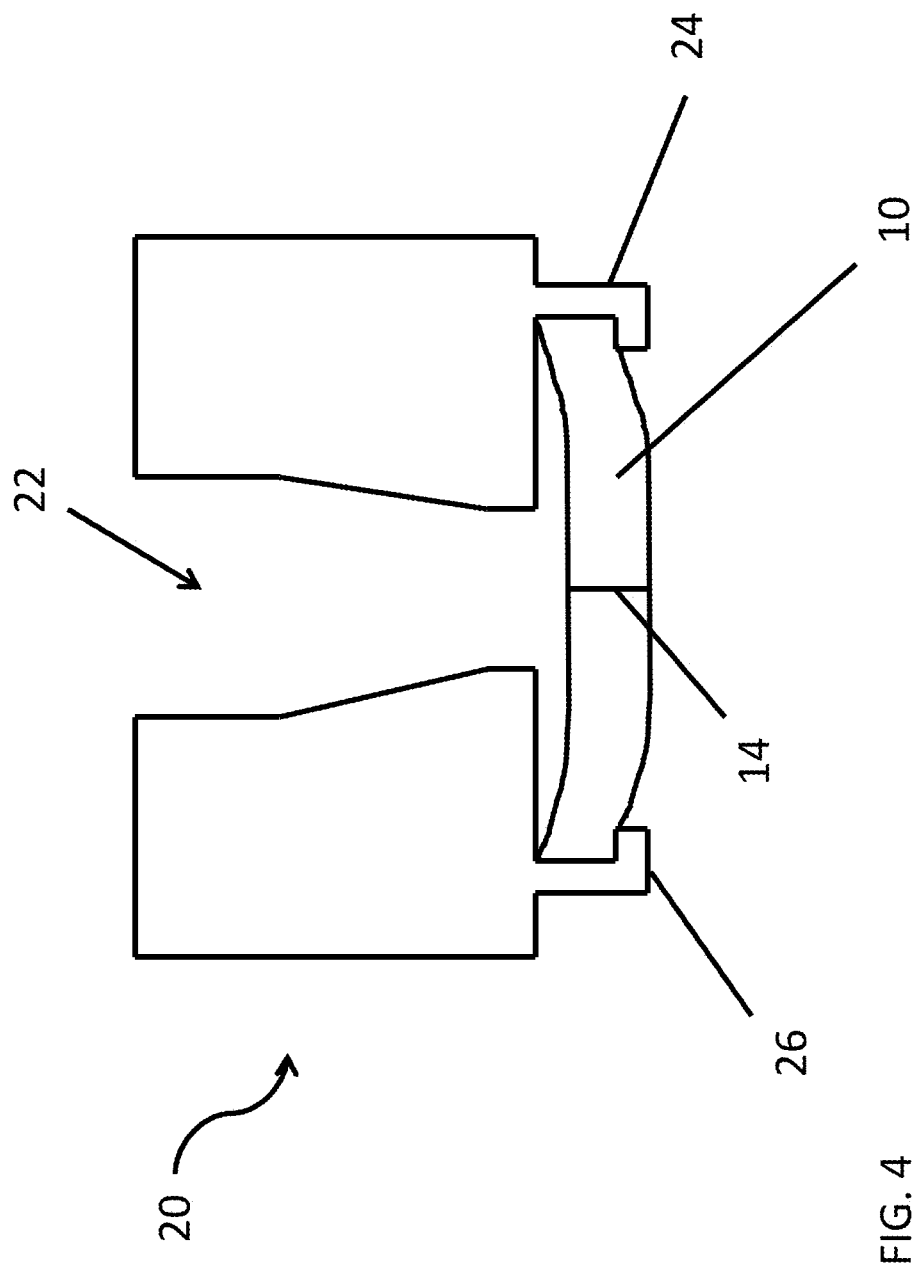
FIG. 4 is a schematic depiction of a septum mounted on a compression block, in accordance with an embodiment of the invention.

A partial assembly of the injection port is shown in FIG. 4, in which the compression block 20 with the septum 10 is mounted in the septum retainer 24. Because in the illustrated embodiment the diameter $d_{10}$ of the septum 10 is greater than the diameter $d_{24}$ of the septum retainer, and because the septum is formed from a flexible, resilient material, it is forced to bow outward from the bottom of the compression block. Moreover, the difference in diameters of the septum and the septum retainer results in the perforation closing naturally when not in use. This feature is further assisted by optional pressure application on a lower side of the septum, as discussed below.

A fully assembled liquid injection port is shown in FIGS. 5a and 5b. In FIG. 5a, the compression block 20 with the septum 10 mounted in the septum retainer 24 has been fitted to the liquid input block 30, with the compression block 20 being adapted to mate with a top surface of the liquid input block. The pipette conduit 22 aligns with the liquid conduit 32. The outer surface of the septum retainer 24 is held in the retainer seat 34, and the septum 10 forms a seal with the liquid input block 30 at the sealing surface 36 between the compression block and the liquid input block. It is noted, however, that because the septum 10 is now compressed between the compression block 20 and the liquid input block 30, it no longer bows outward from the septum retainer. Rather, excess septum material, resulting from the septum diameter $d_{10}$ being greater that the diameter $d_{24}$ of the septum retainer forms a conical depression 16 at the perforation site 14 extending into the liquid input conduit 32. In FIG. 5a, a pipette tip 40 is present in pipette conduit 22, but the tip has not made contact with the septum.

Referring to FIG. 5b, the pipette tip 40 passes through the septum at the perforation site, such that a pipette seal 38 is formed at the surfaces of the septum 10 contacting the pipette tip 40. Liquid may be injected into the liquid input conduit 32 via the pipette tip 40 through the perforation 14 while still maintaining a seal between the pipette conduit 22 and the liquid input conduit 32. Additionally, the conical depression 16 serves as a positioning guide for the pipette tip 40, thereby helping the pipette tip remain centered in the liquid input conduit 32.

Figure 6A:
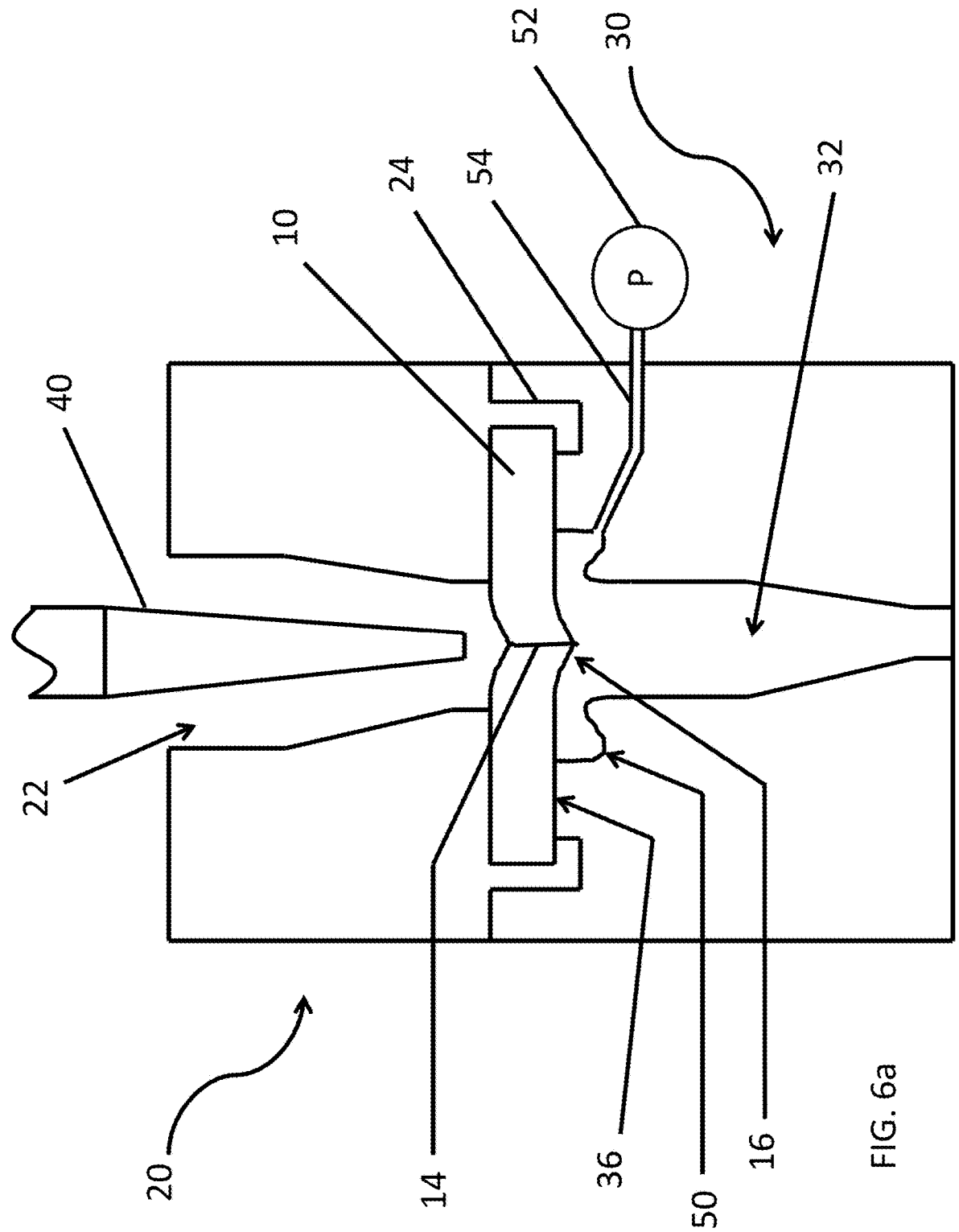
FIG. 6a is a schematic depiction of a second embodiment of a liquid injection port having a pressurization region, in accordance with the present invention.

A second embodiment of the invention is depicted in FIGS. 6a and 6b. In FIG. 6a, the liquid input block 30 is modified to include a circular groove 50 at the top of the liquid input conduit 32. The groove 50 communicates with an external pressure source 52, e.g., a pressurized fluid source, via pressure conduit 54. The pressure source may be house air regulated by a centralized air compressor system or a small piston or diaphragm air compressor such as the KNF Mini Swing Piston Pump or the Hargraves BTC Diaphragm Pumps that can generate up to 30 psi, separated by an air solenoid, so that it does not get wet. The pressure source 52 is thus in fluidic communication with the liquid input conduit 32 and thereby allows the use of a liquid or gas to provide positive pressure to the liquid input conduit 32. Thus, a driving force may be provided to facilitate moving material that has been injected into the liquid input conduit.

Referring to FIG. 6b, pipette tip 40 passes through the septum at the perforation site, such that a pipette seal 38 is formed at the surfaces of the septum 10 contacting the pipette tip 40. A pressurized fluid, e.g., compressed air or gas such as helium, argon, or nitrogen, or pressurized water, is provided by the external pressure source 52 to a backside of the septum. The pressure may be selected from a range of, e.g., 0 to 100 psi, preferably 30 psi. The injected sample may be pressurized to move it. In some applications, e.g., injection of sample into a semiconductor structure such as a lab-on-a-chip, pressurizing the sample also serves to prime the semiconductor structure, which may have too much back pressure due its small dimensions. The sample may be somewhat pressure sensitive, so a low pressure may be sufficient to move the sample through the small passages. This driving force facilitates movement of material into and through the liquid input conduit 32. Moreover, after removal of the pipette tip from the perforation site, positive pressure on the septum helps the perforation site heal itself, thereby minimizing the possibility of leakage. In some embodiments, if the pipette tip is inserted deep enough, the septum contacts a raised lip 56 in the liquid input block 30, proximate the liquid input conduit 32, creating a seal that prevents liquid from entering a pressure supply path 54 leading to the pressure source.

EQUIVALENTS

Those skilled in the art will readily appreciate that all parameters listed herein are meant to be exemplary and actual parameters depend upon the specific application for which the methods and materials of embodiments of the present invention are used. It is, therefore, to be understood that the foregoing embodiments are presented by way of example only and that, within the scope of the appended claims and equivalents thereto, the invention may be practiced otherwise than as specifically described. The described embodiments of the invention, therefore, are intended to be merely exemplary and numerous variations and modifications will be apparent to those skilled in the art. All such variations and modifications are intended to be within the scope of the present invention as defined in the appended claims.

What is claimed is:

1. A liquid injection port for a liquid processing device, the liquid injection port comprising:
   a) a liquid input block defining a liquid input conduit;
   b) a compression block comprising a surface adapted to contact a topmost surface of the liquid input block, the compression block
      i) defining a pipette conduit therethrough vertically aligned with the liquid input conduit; and
      ii) comprising a septum retainer having an internal diameter, wherein the septum retainer extends downward from a bottom portion of the compression block and comprises a wall defining a retention lip at an end thereof; and
   c) a septum mounted in the septum retainer between the pipette conduit and the liquid input conduit, the septum comprising a deformable material and including a central self-healing perforation therethrough to allow a fluid to be introduced across the perforation
   wherein
      i) the septum forms a seal between the liquid input block and the compression block,
      ii) when mounted in the septum retainer, the septum defines, at the central perforation, a conical deformation toward the liquid input conduit while maintaining a seal between the liquid input conduit and the pipette conduit,
      iii) at least a portion of the pipette conduit is cylindrical,
      iv) the central self-healing perforation is defined by deforming the septum without removal of the deformable material from the septum such that the perforation seals closed when an instrument making the perforation is removed, and v) the retention lip of the septum retainer extends underneath the septum.

2. The liquid injection port of claim 1, wherein the septum has a diameter larger than the internal diameter of the septum retainer.

3. The liquid injection port of claim 1, wherein a deformability of the septum and a definition of the central perforation without removal of material enable a pipette tip to pass through the septum to allow introduction of a liquid into the liquid input conduit while maintaining a seal between the pipette tip and sidewalls of the central perforation.

4. The liquid injection port of claim 1, wherein the deformable material comprises an elastomeric material.

5. The liquid injection port of claim 4, wherein the deformable material comprises silicone.

6. The liquid injection port of claim 1, further comprising a pressurized fluid source, in fluidic communication with a backside of the septum.

7. The liquid injection port of claim 6, wherein the pressurized fluid source is adapted to deliver up to 100 psi of a pressurized fluid to the backside of the septum.

8. The liquid injection port of claim 6, wherein the pressurized fluid source is adapted to deliver a pressurized fluid selected from the group consisting of compressed air, helium, nitrogen, argon, and water to the backside of the septum.

9. A method for delivering a fluid from a pipette tip, the method comprising the steps of:
  A) introducing the fluid into the pipette tip;
  B) inserting the pipette tip into a pipette conduit defined by a compression block of a liquid injection port for a liquid processing device, the liquid injection port comprising
    a) a liquid input block defining a liquid input conduit;
    b) the compression block comprising a surface adapted to contact a topmost surface of the liquid input block, the compression block
      i) defining a pipette conduit therethrough vertically aligned with the liquid input conduit; and
      ii) comprising a septum retainer having an internal diameter, wherein the septum retainer extends downward from a bottom portion of the compression block and comprises a wall defining a retention lip at an end thereof; and
    c) a septum mounted in the retention lip of the septum retainer between the pipette conduit and the liquid input conduit, the septum comprising a deformable material and including a central perforation therethrough to allow a fluid to be introduced across the perforation
    wherein
      i) the septum forms a seal between the liquid input block and the compression block,
      ii) when mounted in the septum retainer, the septum defines, at the central perforation, a conical deformation toward the liquid input conduit while maintaining a seal between the liquid input conduit and the pipette conduit,
      iii) at least a portion of the pipette conduit is cylindrical,
      iv) the central self-healing perforation is defined by deforming the septum without removal of the deformable material from the septum such that the perforation seals closed when an instrument making the perforation is removed, and
      v) the retention lip of the septum retainer extends underneath the septum;
  C) inserting the pipette tip through the central perforation defined by the septum; and
  D) releasing the fluid in the pipette tip into the liquid input conduit defined in the liquid input block.

10. The method of claim 9, wherein the pipette tip forms a seal with the perforation when inserted through the perforation.

11. The method of claim 9, further comprising, after releasing the fluid, withdrawing the pipette tip from the perforation, wherein the perforation heals after the pipette tip is withdrawn.

12. The method of claim 9, further comprising:
  (i) withdrawing the pipette tip from the perforation after releasing the fluid; and
  (ii) repeating steps A-D.

13. The method of claim 12, wherein repeating steps A-D comprises using a second pipette tip.

14. The method of claim 9, further comprising:
  delivering a pressurized fluid to a backside of the septum to facilitate movement of the fluid into the liquid input conduit.

15. The method of claim 14, wherein the pressurized fluid is selected from the group consisting of compressed air, helium, nitrogen, argon, and water.

16. The liquid injection port of claim 1, wherein at least a portion of the pipette conduit is tapered.

17. The liquid injection port of claim 1, wherein at least a portion of the liquid input conduit is tapered.

* * * * *